United States Patent [19]

Osmers

[11] 4,027,526

[45] June 7, 1977

[54] METHOD AND APPARATUS FOR MAKING MEASUREMENTS RELATED TO THE FIRST NORMAL STRESS FUNCTION OF VISCOELASTIC FLUID MATERIAL

[75] Inventor: Herman R. Osmers, Pittsford, N.Y.

[73] Assignee: University of Rochester, Rochester, N.Y.

[22] Filed: July 8, 1976

[21] Appl. No.: 703,483

[52] U.S. Cl. ..................................... 73/54; 73/60
[51] Int. Cl.² ....................................... G01N 11/04
[58] Field of Search .......................... 73/54, 55, 60

[56] References Cited

UNITED STATES PATENTS

| 2,568,793 | 9/1951 | De Beaumont | 73/60 |
| 3,111,838 | 11/1963 | Bucalo | 73/54 |
| 3,465,575 | 9/1969 | Kepes | 73/60 |

Primary Examiner—Richard C. Queisser
Assistant Examiner—Joseph W. Roskos
Attorney, Agent, or Firm—Martin Lu Kacher

[57] ABSTRACT

The first normal stress function of a viscoelastic material which is a measure of its elasticity and a more sensitive indication of certain other parameters of the material, and process conditions, than the viscosity thereof, is determined from measurements of the thrust in a direction normal to the inner and outer walls of an annular channel in which the viscoelastic fluid material flows under pressure, at high shear rates in an angular direction. These thrust measurements may be made under regulated flow so as to eliminate the need for alignment of the positions at which the thrust measurements are made. The measurement system is closed so that evaporation and degradation of the fluid material as may occur in such systems as are open to the atmosphere are avoided. The first normal stress function may be determined over a broad range of shear rates such as are experienced in polymer processing (e.g., extrusion and injection molding) so as to facilitate continuous or real time process control.

13 Claims, 4 Drawing Figures

U.S. Patent  June 7, 1977  4,027,526
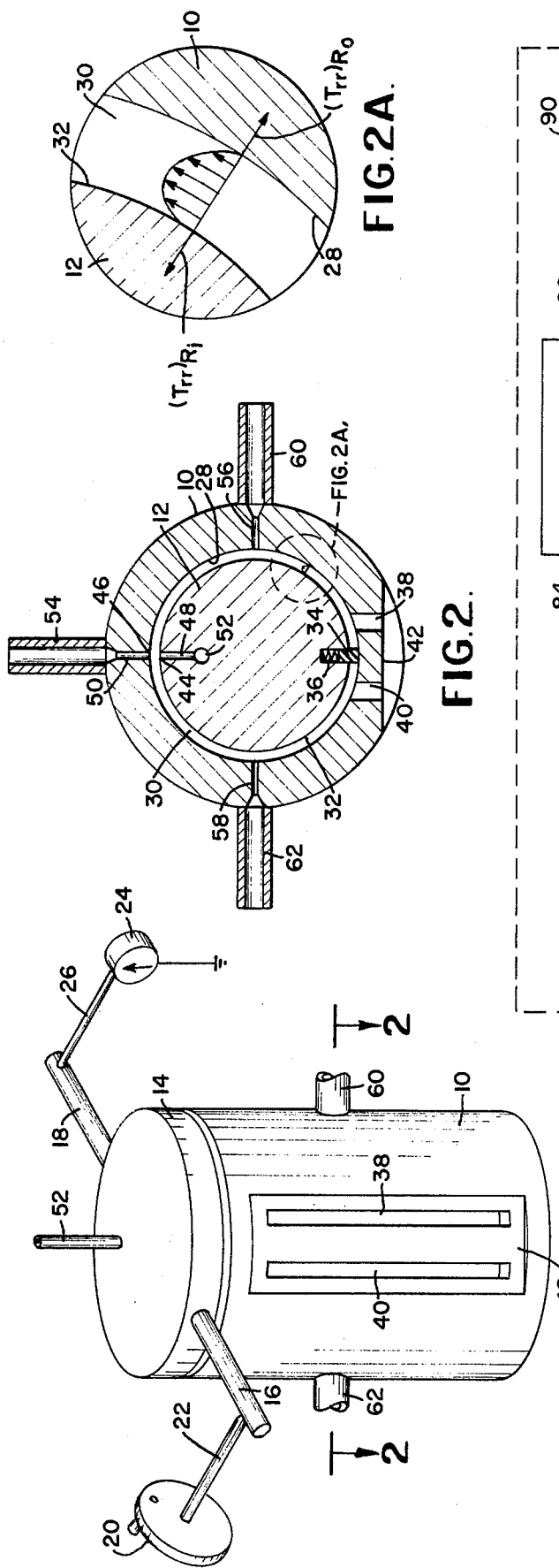
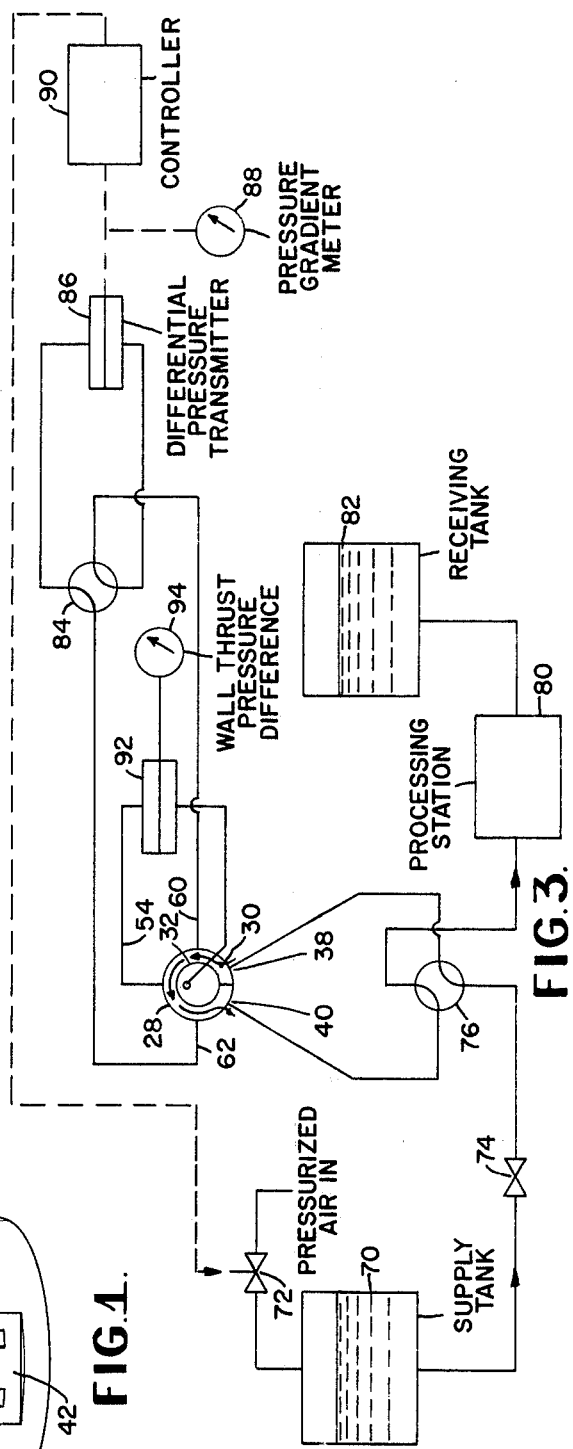

METHOD AND APPARATUS FOR MAKING MEASUREMENTS RELATED TO THE FIRST NORMAL STRESS FUNCTION OF VISCOELASTIC FLUID MATERIAL

The present invention relates to methods of and apparatus for making measurements related to the elasticity of viscoelastic fluid materials and particularly the first normal stress function of viscoelastic fluid materials. The invention herein described was made in the course of or under a contract or subcontract thereunder with the Office of Naval Research, Department of the Navy.

The invention is especially suitable for use in the processing of polymers such as polymer melts and solutions. Features of the invention are however generally applicable for use wherever information respecting elastic behavior, material properties, and process conditions involving viscoelastic fluid materials, is desired. Such material properties include molecular weight parameters.

Wherever viscometric flow of a viscoelastic material occurs, the stresses in the material are related to the flow kinematics by three material functions; namely the viscosity function and the first and second normal stress functions. Viscosity is a measure of the shear rate or deformation rate of the fluid material and is often made between plates or a conical member and a plate which move relative to each other. Various techniques have been suggested for measuring viscosity as a function of the velocity of the plate or otherwise with respect to the motion of the liquid so as to indicate its deformation or shear. Reference may be had to the following United States Patents for such viscosity measurements techniques: Miller, U.S. Pat. No. 1,727,836; Wynn, et al, U.S. Pat. No. 2,198,325; DeBeaumont, U.S. Pat. No. 2,568,793; Martin, U.S. Pat. No. 008,326; Bucalo, U.S. Pat. No. 3,111,838; Erickson, U.S. Pat. No. 3,363,452; Kepes, U.S. Pat. No. 3,465,575; Spitsbergen, U.S. Pat. No. 3,501,948; and Hirs, U.S. Pat. No. 3,504,529.

Viscoelastic effects are manifested by the normal stress function in terms of the stresses exhibited by the material in a direction normal and parallel to the flow direction. Viscosity measurements alone therefore do not reflect these viscoelastic effects because they relate to shearing stress. Moreover, the first normal stress function is a much more sensitive indication of viscoelastic material behavior than the viscosity function, and even the second normal stress function.

Viscoelastic effects, as manifested by the first normal stress function, depend upon the shear rate and may be non-linearly related to shear rate and even the non-linear relationship is not a priori known. Thus, it is not feasible merely to extrapolate measurements of this function at low shear rates. Rather, measurements must be made at high shear rates in order to accurately reflect the first normal stress function under high shear rate conditions. Shear rate ranges depend upon material being processed. For example, high shear rates for polymer melts, as occur in extrusion and injection molding processes are from $10^2$ to $10^3$ sec$^{-1}$. The techniques involving relatively moving surfaces which are used in making viscosity measurements, are limited to relatively low shear rates (e.g., 1 to 10 sec$^{-1}$). This limitation may result from the onset of secondary flows, fractures and stress propagations at the fluid surface interfaces. Techniques which have been previously suggested for measuring the first normal stress function involve the use of capillary rheometers (see Han, Trans. Soc. Rheol., 18, 163 (1974)). Such techniques do not operate at high shear rates continuously for on-line process control. Also such techniques require venting of the system to the atmosphere which can lead to evaporation and degradation of the fluid material. Pressure driven axial flow apparatus has been proposed for the measurement of the second normal stress function (see Lobo and Osmers, Rheol. Acta. 13, 457 (1974)). However, as noted above, the second normal stress function is a far less sensitive indication of viscoelastic behavior and the apparatus for making such measurements is subject to errors, especially at high shear rates.

It is therefore an object of this invention to provide improved methods of and apparatus for making measurements related to the first normal stress function of viscoelastic fluid material.

It is a further object of the present invention to provide improved methods of and apparatus for making measurements related to the first normal stress function of viscoelastic fluid material over a broad range of shear rates including high shear rates as occur in the processing of polymer materials, as by extrusion, injection molding and the like.

It is a still further object of the present invention to provide improved methods of and apparatus for making measurements relating to the first normal stress function of viscoelastic fluid material which permits the use of a totally closed system and thereby avoids evaporation, contamination, or other degradation of the material which may be cuased by exposure thereof to the atmosphere.

It is a still further object of the present invention to provide methods of and apparatus for making measurements related to the first normal stress function of viscoelastic fluid material which may be used on line and in real time for process contrcl purposes.

Briefly described, the method of making measurements related to the first normal stress function of viscoelastic fluid material in accordance with this invention encompasses the steps of driving the fluid material under pressure in an angular direction around an annular channel which may be formed between the walls of two members, one of which may be displaced with respect to the other. It will be noted however, that measurements are not made while members are being displaced but only after displacements have taken place, and such displacement is only for the purpose of eliminating the need to provide alignment of the walls with respect to each other, in order to simplify the making of the measurements.

These measurements involve measuring the pressure due to the thrust exerted in a direction normal to the channel walls. These measurements are related to the first normal stress function. While not restricted thereto, the measurements may be made under conditions of constant flow rate. Since the flow rate is a function of the shear rate of the material, measurements may be made at different flow rates so as to cover the desired shear rate range. Two measurements may be made; first by angularly displacing the members with respect to each other in one direction, and secondly by displacing the members in the opposite direction with respect to each other. The total displacement between the measurement positions is then related to the first normal stress function and the need for aligning the apparatus in the first instance is obviated.

The foregoing and other objects, features and advantages of the invention as well as the mode of operation and the presently preferred embodiment thereof will become more apparent from a reading of the following description in connection with the accompanying drawings in which:

FIG. 1 is a perspective view schematically showing apparatus provided in accordance with the invention for making measurements related to the first normal stress function of viscoelastic fluid material;

FIG. 2 is a sectional view of the apparatus shown in FIG. 1, the section being taken along the line 2—2 in FIG. 1;

FIG. 2a is an enlarged view of a portion of FIG. 1 indicating the flow of the viscoelastic material in the angular direction around the annular channel provided by the apparatus shown in FIGS. 1 and 2; and FIG. 3 is a schematic diagram of the flow and control system utilizing the apparatus shown in FIGS. 1 and 2 which may be used for making measurements related to the first normal stress function of viscoelastic fluid material, as for process control purposes.

Referring to FIGS. 1 and 2, there is shown an outer cylindrical member which may be fixed and an inner cylindrical member 12 which is coaxial with the outer cylindrical member 10 and may be rotated with respect thereto. The upper end 14 of the inner cylinder 12 is enlarged to form a flange which rests upon the upper end of the outer cylinder 10. A pair of arms 16 and 18, which are diametrically opposite from each other, extend outwardly from the upper end 14 of the inner cylinder 12. By rotating a crank 20, a shaft 22 is advanced, as by a worm gear arrangement which couples the crank 20 and the end of the shaft 22 in driving relationship, so as to move the arm 16. The displacement of the inner cylinder 12 is measured by a dial indicator 24 having a sensing shaft 26 which is attached to or biased against the other arm 18.

The inner peripheral surface of the outer cylinder 10 provides a wall 28 of an annular channel 30 of generally tubular shape sealed at both ends. The inner peripheral surface of the inner cylinder 12 provides the opposite wall 32 of this annular channel 30. A vane 34 in a slot 36 in the inner cylinder 12 is spring biased against the outer wall 28 of the channel. Ports 38 and 40 in the outer cylinder 10 provide inlets and outlets for fluid to be introduced into the channel. These ports 38 and 40 are shown as rectangular slits. A manifold (not shown) is attached to the outer cylinder 10 at 42 so as to provide a connection for fluid lines to the ports 38 and 40.

The fluid material is pressurized so as to flow between the ports 38 and 40 under pressure over an angular path (viz., an angular flow path along the channel 30 for the fluid material). This flow may be in the clockwise or counter-clockwise direction, as will be explained more fully hereinafter. Flow in the clockwise direction is shown in FIG. 2a which indicates the fluid velocity profile by the arrows. The flow is laminar and has the highest velocity displaced from the center of the channel 30 towards the inner wall 32 inasmuch as the inner wall 32 is of slightly smaller diameter than the outer wall 28.

Because it is viscoelastic the fluid exerts a normal stress or thrust against the walls 28 and 30. This normal thrust is indicated by the arrows $(T_{rr})\ R_o$ against the outer wall 28 and $(T_{rr})\ R_i$ against the inner wall 32. It is by measuring these thrusts that measurements related to the first normal stress function may be obtained. It can be shown that $$\Delta T_{rr} \equiv (T_{rr})\ R_o - (T_{rr})\ R_i \approx \int_{R_i}^{R_o} \frac{N_1(\tau)}{r} dr, \quad (1)$$

where $N_1$ is the first normal stress function. $\tau$ is the shear stress component and $r$ is distance in the radial direction measured from the center line of the cylinders 10 and 12.

Returning to FIGS. 1 and 2, provision is made for measuring this normal thrust. A pressure tap 44 is provided at the inner wall 32 and another pressure tap 46 is provided at the outer wall 28. These pressure taps consists of channels 48 and 50 which extend normal to the walls 32 and 28. These channels may be small lines of a diameter, for example, of about 0.03 inch. The channel 48 is brought out of the apparatus through a line 52 which is in communication therewith. Another line 54 which extends outwardly from the outer wall of the outer cylinder 10 is in communication with the channel 50. As will be explained more fully hereinafter, the thrust measurement is made by measuring the pressures exerted by the fluid in the channel 30 in a direction normal to the walls 28 and 32. The transducers for measuring this pressure may be disposed outside of the cylinders 10 and 12 and connected thereto by means of the lines 52 and 54. It may however be desirable to utilize small pressure transducers which may be inserted directly at the walls 28 and 32 in the positions occupied by the taps 44 and 46, i.e., flush with the walls 28 and 32. Then electrical leads are brought out from these transducers rather than lines which communicate the fluid through external transducers.

For measuring and controlling the rate of flow of the fluid along the angular path in the channel 30, there are provided pressure taps 56 and 58, which are shown at diametrically opposed locations on the outer wall 28, but which may be at other angular displacements. These pressure taps are in the form of channels which lead to lines 60 and 62. By measuring the difference in pressure at the taps 56 and 58 the angular pressure gradient may also be determined. This pressure gradient is a function of the shear rate. Thus by increasing the angular pressure on the fluid, the flow rate and the shear rate may be increased and measurements across the entire range of shear rates which are desired may be made by varying the pressure under which the fluid is introduced through the channel 30.

In operation, a differential pressure transmitter 92 (a device which provides an output proportional to the difference in pressure inputs) may be connected across the lines 52 and 54 and thus measures the difference in pressure in a direction normal to the walls 28 and 32 at the taps 44 and 46. At a desired flow rate, as may be adjusted by varying the pressure drop across the ports 38 and 40 by means of another differential pressure transmitter 86 connected between the lines 60 and 62, the inner cylinder 12 can be rotated down stream until equal pressures are sensed at the pressure taps 44 and 46 (i.e., the output of the pressure transmitter 92 which may be a capacitance bridge null meter coupled to the channels 52 and 54, indicates a zero or null condition). The difference in the thrusts in the normal direction against the walls 28 and 32 is now balanced against the pressure difference given by the product of the pressure gradient along the angular flow path and the angular rotation or angular displacement. This angular displacement is introduced by means of the crank 20 and is measured on the dial indicator 24. Since the positions of the taps 44 and 46 may not be known (viz., they may not have initially been aligned with each other), the direction of flow is reversed at the same flow rate (identical pressure gradient) as measured by the transmitter 86, connected to the lines 60 and 62. The inner cylinder is then displaced, using the crank 20, in the new down stream direction and a second null position is obtained. The total angular displacement between the two null positions $\theta$ is measured in terms of the displacement indicated on the dial indicator 24, and can be used to provide an output related to the wall thrust difference for the angular pressure gradient $dP/d\theta$ by the expression $$(\Delta T_{rr}) = -\frac{\theta(dP/d\theta)}{2} \qquad (2)$$

In the event that flush pressure transducers are used at the tap locations 44 and 46 and aligned along the same radial line, then $\Delta T_{rr}$ may be measured directly and without the need for angular displacement of the inner cylinder 12. Then the pressure taps 56 and 58 need not be provided so long as other means for flow measurement and regulation are provided.

Referring to FIG. 3, the angular annular flow path for the fluid material is shown in the channel 30. The fluid is introduced into the channel from a supply tank 70. This is a closed tank which is pressurized by high pressure air which is applied to the top of the tank 70 through a control valve 72. The fluid from the tank passes through a shutoff valve 74 and thence through a four-way valve 76 to the port 38 which serves as a supply or inlet port when the valve 76 is in the position shown. The port 40 then serves as a return or outlet port and fluid from the channel passes through the valve 76 to a processing station 80 (e.g., an extruder or injection molding apparatus when the fluid is a polymer melt). The excess material then passes from the processing station 80 to a receiving tank 82. The material which passes through the processing station may alternatively be returned to the supply tank 70 or discharged.

The angular pressure gradient is determined by connecting the lines 60 and 62 through another four-way valve 84 to a differential pressure or pressure gradient transmitter 86. The differential pressure transmitter 86 translates the pressure difference as measured at the ends of the lines 60 and 62 into an output pneumatic control pressure. The differential pressure transmitter 86 may receive a supply of pressurized air from an inlet line (not shown) so as to develop this pneumatic control pressure. Electrical or other control may also be used.

The pneumatic output line from the transmitter 86 is connected to a pressure gradient meter 88 for purposes of monitoring this pressure. The line is then connected to a controller 90 which may be a pneumatic servo motor which applies an output pressure for controlling the valve 72. The controller 90 is set so as to provide control pressure in opposite directions corresponding to changes in the pressure gradient as sensed by the transmitter 86. Accordingly, the supply pressure of the fluid material as it is introduced into the annular channel 30 is maintained at the selected pressure which corresponds to the selected flow rate. The flow rate may be adjusted by changing the setting on the controller. In this way different flow rates may be selected so that measurements of the first normal stress function at different shear rates may be obtained.

The measurements related to the first normal stress function are obtained by means of the pressure gradient transmitter 92, the output of which is coupled to a pressure difference meter 94, which may be a capacitive null meter as discussed above. This transmitter 92 is connected by way of the lines 52 and 54 to the pressure taps 44 and 46.

As indicated above the flow direction through the annular channel 30 is changed through the use of a four-way valve 76. When the direction of flow is changed, the other four-way valve 84 is actuated (both valves 76 and 84 may be ganged or actuated together, if desired) and as soon as the system has settled the inner cylinder 12 may be displaced in the opposite direction and the second measurement made. The angular displacement of the inner cylinder between the positions where the measurements are made is used to provide the first normal stress function measurement as explained above.

It will be noted that the measurement system is entirely enclosed so that evaporation, contamination, or other degradation of the fluid material is avoided and material losses may be eliminated.

The value of the first normal stress function $N_1$ (see equation (1) above) may be derived precisely from the measurements. Reference may be had to Osmers et al, Trans. Soc. Rheol. 20:2, 239–252 (1976) for techniques which may be used to derive $N_1$ from these measurements.

From the foregoing description it will be apparent that there has been provided an improved method of and apparatus for making measurements related to the first normal stress function of viscoelastic materials. While presently preferred embodiments of the method and apparatus have been described herein, it will be appreciated that variations and modifications therein within the scope of the invention will undoubtedly suggest themselves to those skilled in the art. Accordingly, the foregoing description should be taken as illustrative and not in any limiting sense.

What is claimed is:

1. The method of making a measurement related to the first normal stress function of a viscoelastic fluid material which comprises the steps of driving said fluid material under pressure in an angular direction around an annular channel formed between opposing walls, and measuring the pressure due to the thrust exerted in a direction normal to said channel against each of said opposing walls, said pressure measurements being related to said first normal stress function.

2. The invention as set forth in claim 1 including the step of obtaining the difference in said pressure thereby providing said measurement related to said first normal stress function.

3. The invention as set forth in claim 2 wherein said driving step includes the step of regulating the flow of said material through said annular channel at a substantially constant rate.

4. The invention as set forth in claim 3 wherein said measuring step is carried out by angularly displacing one of said walls of said channel in opposite directions with respect to the other of said walls and measuring each of said displacements which correspond to like pressures, and deriving from said displacements the measurement related to said first normal stress function.

5. Apparatus for making measurements related to the first normal stress function of a viscoelastic fluid material which comprises first and second members having opposed walls which define an annular channel defining an angular path extending circumferentially about said first member, means for introducing said fluid medium under pressure into said channel to flow through said channel along said angular path, and means for measuring the thrusts exerted by said liquid against each of said walls whereby to provide said measurements.

6. The invention as set forth in claim 5 wherein said thrust measuring means are means for measuring the pressure of said liquid in a direction normal to said walls.

7. The invention as set forth in claim 6 wherein said pressure measuring means include second and third channels extending in a direction normal to said first and second member walls respectively, and pressure measuring devices in communication with said third and fourth channels.

8. The invention as set forth in claim 7 wherein said pressure measurement means includes means for measuring the difference in said pressure.

9. The invention as set forth in claim 5 wherein one of said first and second members is movable with respect to the other thereof, and wherein said measuring means includes means for displacing of said members in opposite directions with respect to each other, means for measuring the difference between said thrusts, and means for measuring the displacement of said members in each of said directions for equal magnitudes of said difference between said thrusts, said displacements being the measurements related to said first normal stress function.

10. The invention as set forth in claim 9 wherein said thrust measuring means includes means communicating with said walls for measuring the pressure of said fluid material in directions normal to said walls.

11. The invention as set forth in claim 10 including means for regulating the flow through said channel so that the flow remains constant while said measurements are made.

12. The invention as set forth in claim 11 wherein said flow regulating means includes means for measuring the pressure of said fluid in said channel at positions angularly displaced from each other and on opposite sides of the portion of said channel where said thrust measurements are made, and means responsive to said last-named pressure measurements for varying the pressure under which said fluid material is introduced into said channel.

13. The invention as set forth in claim 12 wherein said first member is a first cylinder, said second member is a second cylinder, the outer peripheral surface of said first cylinder being one of said opposed walls, the inner peripheral surface of said second cylinder being the other of said opposed walls, said walls being radially spaced from each other to define said annular channel therebetween, a vane extending radially between said walls, and said introducing means including inlet and outlet ports on opposite sides of said vane in communication with said channel such that said fluid material flows along said angular path about said channel between said ports.

* * * * *